United States Patent [19]

Mays et al.

[11] Patent Number: 4,794,080

[45] Date of Patent: Dec. 27, 1988

[54] MICROBIAL CO-CULTURE PRODUCTION OF PROPIONIC ACID

[75] Inventors: Thomas D. Mays, Burtonsville; Pamela N. Fornili, Annapolis, both of Md.

[73] Assignee: IGENE Biotechnology, Inc., Columbia, Md.

[21] Appl. No.: 600,824

[22] Filed: Apr. 16, 1984

[51] Int. Cl.⁴ .................. C12P 39/00; C12P 7/54; C12P 7/52; C12N 1/20

[52] U.S. Cl. .................. 435/42; 435/140; 435/141; 435/822; 435/853; 435/885; 435/801; 435/139; 435/252.4

[58] Field of Search .................. 435/42, 141, 253, 822, 435/826

[56] References Cited

U.S. PATENT DOCUMENTS

| | | | |
|---|---|---|---|
| 1,932,755 | 10/1933 | Stiles et al. | 435/42 |
| 4,391,887 | 7/1983 | Baumgarton et al. | 435/42 |
| 4,567,140 | 1/1986 | Voelskow et al. | 435/42 |

OTHER PUBLICATIONS

Liu et al., 1982, Appl. Environ. Microbiol 44/3/715-722.

Bergey's Manual of Systemic Bacteriology Krieg et al. (eds) 1984, Williams and Wilkins, Baltimore.

Distler, W. and A. Kroncke, "Acid Formation by Mixed Cultures of Dental Plaque Bacteria Actinomyces and Veillonella", Arch. Oral Biol., vol. 26, pp. 123–136 (1981).

*Primary Examiner*—Elizabeth Weimar
*Assistant Examiner*—Richard C. Peet
*Attorney, Agent, or Firm*—Haight & Associates

[57] ABSTRACT

A simultaneous sequential anaerobic fermentation process for the in vitro production of propionic and acetic acids is disclosed. The process comprises employing an obligatory two-component co-culture which maintains a relatively constant ratio of species populations over multiple passages. A first co-culture component is a Lactobacillus or Streptococcus which homofermentatively converts the hexose to lactic acid. A second microorganism in the co-culture is a Veillonella which is metabolically incapable of assimillating the hexose and converts the lactic acid product to propionic and acetic acids. The co-culture is inoculated into a nutrient growth feedstock such as whole whey or a clarified dairy whey lactose permeate which contains a metabolizable source of a hexose such as glucose, lactose or sucrose.

14 Claims, No Drawings

MICROBIAL CO-CULTURE PRODUCTION OF PROPIONIC ACID

DESCRIPTION OF THE INVENTION

1. Technical Field of the Invention

This invention relates to a process for the production of lactic acid or its salts and propionic acid and/or acetic acid or its salts by the catabolism of carbohydrate feedstocks utilizing a simultaneous two-stage bacterial fermentation process. In a first stage, carbohydrates are converted to lactic acid, e.g. by saccharolytic bacteria such as *Lactobacillus casei* subspecies *rhamnosus*. In a second stage, the resultant lactic acid is fermented to propionic and acetic acids, carbon dioxide and hydrogen by a second bacterium which is adapted to grow in the presence of the first bacterium, e.g. by a lactic acid-catabolizing bacterium such as *Veillonella criceti*.

2. Background Art

Propionic acid is used commercially as an esterifying agent, in the production of cellulose propionate (a thermoplastic), and as a naturally occurring bacterial fermentation metabolite in cheese and other dairy products. Salt forms of the free acid such as calcium or sodium propionate are used as preservatives in food products to inhibit fungal growth, as well as and in manufacturing ester solvents, fruit flavors, and perfume bases.

Traditional means of producing propionic acid have been via bacterial fermentation using strains of the genus Propionibacterium, e.g. see U.S. Pat. Nos. 1,459,959; 1,865,146; 1,875,401; 1,898,329; 1,913,346; 1,932,755; and 3,067,107. In the past 30 to 40 years, chemical processes such as condensation of carbon monoxide and ethylene or ethanol have proven economically feasible. However, recent increases in the cost of petrochemical feedstocks have resulted in a reexamination of biological and agricultural feedstocks for the manufacture of many chemicals including propionic acid.

Propionibacteria of the genus Propionibacterium have traditionally been used for propionic acid production by bacterial fermentation. However, use of Propionibacterium species in monoculture or in co-culture with strains of Lactobacillus has generally resulted in either lower levels of propionic acid, long fermenter residence periods, or both. These limitations may result from a long lag period preceding the growth of Propionibacteria, inhibition of growth of Propionibacteria by propionic acid or, in the case of co-cultivation with lactic acid-producing species of Lactobacillus, from the preferential catabolism of carbohydrate by Propionibacterium species over the fermentation of lactic acid to propionic acid.

DISCLOSURE OF THE INVENTION

Accordingly, it is a general object of the present invention to provide a process for the microbial co-culture of propionic acid in high yields.

Another object of the present invention is to provide such a process which provides high yields in dramatically shorter fermenter residence periods.

A further object of the present invention is to provide such a process wherein the lactic acid metabolic product of one microorganism serves as a feedback for the production of propionic acid by a second microorganism.

An additional object of the present invention is to provide such a process which converts a major portion of lactic acid from a variety of feedstocks into propionic acid.

A more particular object of the present invention is to provide a novel co-culture of microorganisms for use in such a process.

Upon study of the specification and appended claims, further objects, features and advantages of the present invention will become more fully apparent to those skilled in the art to which this invention pertains.

BEST MODE FOR CARRYING OUT THE INVENTION

Briefly, the above and other objects, features and advantages of the present invention are attained in one aspect thereof by providing a process for the in vitro production of lactic acid by fermentation of a nutrient growth medium feedstock containing a source of assimilable carbohydrates, e.g., a hepose or pentose, with a first microorganism capable of converting said carbohydrates to lactic acid under nutrient growth conditions, wherein the fermentation is conducted in the additional presence of a second microorganism which is adapted to grow in co-culture with the first microorganism and which converts a major portion of the lactic acid fermentation product into a compound selected from the group consisting of propionic acid, acetic acid, and salts and mixtures thereof.

Suitable feedstocks for the microbial production of lactic acid are well known in the art and include but are not limited to those described in the foregoing U.S. Patents and numerous other publications, e.g. see M. Brin, *Biochem. Prepn.* 3:61 (1953); S. C. Prescott et al., *Industrial Microbiology* (McGraw-Hill, New York, 3rd ed., 1959) pp. 304–331; Andersen et al., *Ind. Eng. Chem.* 34: 1522 (1942); and M. Brin et al., *Ann. N.Y. Acad. Sci.* 119: 851–1165 (1965). For commercial applications, feedstocks such as whey, cornstarch, potatoes, and molasses are generally preferred. The presently preferred feedstocks comprise whole whey or a clarified dairy whey lactose permeate, especially that described and claimed in PCT International Publication Number WO 84/01104 published Mar. 29, 1984, the contents of which are incorporated by reference herein.

The choice of a microorganism for producing lactic acid for use in accordance with the present invention will of course depend on the particular feedstock components to be converted to lactic acid, for which many suitable microorganisms are well known in the art. Because clarified dairy whey lactose permeate is the presently preferred feedstock for use in the present invention, *Lactobarillus casei* is the presently preferred microorganism for the first stage of the instant process, especially *Lactobacillus casei* subsp. *rhamnosus*. Such strains are widely known and readily available to those skilled in the art, e.g. from the American Type Culture Collection (ATCC), 12301 Parklawn Drive, Rockville, Md. 20852.

The choice of a second microorganism for converting the lactic acid metabolic product of the first microorganism into propionic acid requires the selection of a microorganism having the ability to ferment lactic acid into propionic acid and other end products. Several such bacteria are well known and widely available in the art for such purposes, e.g. as has been described in British Pat. No. 1,251,483; U.S. Pat. Nos. 3,857,971 and 4,138,498; and by Huber et al. in *Am. J. Vet. Res.* 37(5):

611–613 (1976). Such bacteria are well known and widely available to those skilled in the art, and include but are not limited to *Megasphaera elsdenii, Peptococcus asaccharolyticus, Selenomonas ruminatium,* and *Veillonella criceti.* Especially suitable for use in the present invention are those microorganisms which preferentially use lactic acid as a source of assimilable carbohydrate; because they exhibit this property (with the exception of fructose, *V. criceti* appears incapable of fermenting carbohydrates directly, presumably due to the lack of hexokinase enzymes, and instead utilities monocarboxylic acids such as lactic acid as a growth substrate) and do not exhibit a long lag period preceding the rapid growth phase in vitro, *Veillonella criceti* is presently preferred.

The sequential treatment of feedstock to first form lactic acid and then form propioic acid suffers from a number of inherent difficulties. In the first stage, the accumulation of lactic acid product eventually slows the feedstock conversion due to mass balance effects and lowering of the pH. While the latter can be adjusted, this introduces an additional risk of contamination whereas removal of lactic acid product involves removing both unconverted feedstock and the converting microorganism. In the second stage, an undesired lactate concentration will remain if the pH is not controlled, and introducing unconverted feedstock provides an opportunity for the microorganism to employ metabolic pathways leading to the formation of undesired products.

In accordance with the present invention, it has now been found that the above and otherdifficulties can be overcome by the catabolism of carbohydrates using a simultaneous two-stage bacterial fermentation process. In the first stage, carbohydrates are converted to lactic acid by the saccharolytic bacterium, *L. casei* subspecies *rhamnosus*. In the second stage, the resultant lactic acid is fermented to propionic and acetic acids, carbon dioxide and hydrogen by *V. criceti*. Propionate (and lactate) thus formed may be recovered by the use of an appropriate solvent extraction system, a distillation recovery process, cationic salt formation with precipitation, or by the concentration and drying of the fermentation broth medium (with or without the removal of the bacterial cells.)

Formation of co-culture

Parent strains of ClS917 (*Lactobacillus casei* subspecies *rhamnosus*) and 1218 (*Veillonella criceti*) were separately selected from spontaneous antibiotic resistant colonies growing on streptomycin and rifampicin (for *L. casei*) or rifampicin alone (for *V. criceti*). These mutant strains of *L. casei* and *V. criceti*, bearing genetic markers (i.e. resistance to specific antibiotics), were then tested for acid products of metabolism in a tryptone broth medium which has the following composition (values expressed as final concentrations on a weight/weight basis): tryptone, (10%); yeast extract, (1.0%); sodium lactate, (2.0%); cysteine hydrochloride, (0.5%); and sodium bicarbonate, (0.5%). Those mutant strains (CLS917 and 1218) demonstrating maximum acid production were then selected.

These broth cultures were incubated anaerobically for 24 hours at separate temperatures to determine the optimum for stable growth of both strains. The optimum temperature was determined to be 38° C. estimated by the number of viable cells of each strain.

Viable and healthy bacterial cells of both mutant strains were added to a chopped meat broth culture medium prepared as described by Holdeman and Moore, *Anaerobe Laboratory Manual,* 4th edition, Department of Anaerobic Microbiology, Virginia Polytechnic Institute and State University, Blacksburg, Va., 24061. Serial passage of the co-culture by transfer and subcultivation at 24 hour periods over a three day interval demonstrated a stable mixed two member bacterial culture (see Table 1). The stability of the co-culture was determined by the enumeration of the two bacterial population for each chopped meat broth culture. This was accomplished using the standard technique of a solid growth medium inoculated with serial dilutions of the broth cultures. The solid growth medium comprised the previously described tryptone broth medium with the addition of agar agar to a final concentration of 1.5%. The pH of the solid medium was adjusted before steam sterilization to 7.0 ( and was observed to be 6.8 to 7.0 following sterilization.) The diluent for preparation of the serial dilutions was that described in the *Anaerobe Laboratory Manual,* 4th edition. Subcultures were incubated for 24 hours before the populations were enumerated. The co-culture is considered stable when the ratio of the two organisms remains constant within the limits of experimental error, demonstrating that neither organism is overtaking the other.

TABLE I

| | STABILITY OF CO-CULTURE | | |
|---|---|---|---|
| Subculture Transfer No.: | Population of strain CLS917 | Population of strain 1218 | Ratio of CLS917:1218 |
| | (values expressed as $10^5$ cells per milliliter) | | |
| 0 (Initial inoculum) | 78 | 142 | 0.55 |
| 1 | 850 | 1500 | 0.57 |
| 2 | 630 | 1000 | 0.63 |
| 3 | 730 | 1500 | 0.49 |

The size of the viable cell population of *L. casei* strain CLS917 in the inoculum at the start of the experimet was approximately one-half the size of the population of the *V. criceti* strain 1218. At the end of each of the three days, the ratio of these two populations was relatively constant. Further use of a single chopped meat broth co-culture as an inoculum for fifteen separate three-liter batch fermentations over a two month period resulted in mixed populations of similar viable cell proportions.

Maintenance of the co-culture

The co-culture can be maintained in sealed vials in aliquots of 0.2 milliliters containing equal volumes of sterile glycerol and tryptone broth culture medium (previously described) at a temperature of −80° C. Each aliquot should contain equal numbers of both strains (approximatly one hundred million bacterial cells each) previously harvested from healthy growing cultures. This co-culture of *Lactobacillus casei* subsp. *rhamnosus* and *Veillonella criceti* has been deposited with the American Type Culture Collection on Apr. 9, 1984 has been designated ATCC Deposit No. 39,662. The strains may be revived following storage by inoculation of the contents into either tryptone or chopped meat broth medium and incubated under anaerobic conditions at 38° C. for 24 to 48 hours.

Production and use of metabolic products

The metabolism of a fermentable carbohydrate in a suitable nutrient medium by strains of Lactobacillus results in the production of low levels of acetate and high levels of lactate. The lactate is then rapidly metabolized by strains of Veillonella present in the co-culture into propionate, acetate, carbon dioxide and hydrogen. Table 2 illustrates part of the array of carbohydrate substrates that can be fermented into propionate, acetate, carbon dioxide, hydrogen and lactate by the co-cultivation of strains of Lactobacillus and Veillonella.

TABLE 2

| | ACID PRODUCTION (MG/ML) AFTER 72 HOURS OF CULTIVATION* | | | | | | | | |
|---|---|---|---|---|---|---|---|---|---|
| | V. criceti (1218) | | | L. casei (CLS917) | | | CO-CULTURE | | |
| CARBOHYDRATE: | ACET | PROP | LACT | ACET | PROP | LACT | ACET | PROP | LACT |
| CONTROL (WATER) | 0.34 | 0.79 | ND | ND | ND | 0.30 | 0.46 | 0.95 | ND |
| CELLOBIOSE | 0.36 | 0.75 | ND | 0.18 | ND | 7.40 | 3.11 | 3.92 | 1.03 |
| FRUCTOSE | 2.24 | 2.85 | ND | ND | ND | 0.26 | 2.94 | 4.02 | 0.47 |
| GALACTOSE | 0.37 | 0.70 | ND | ND | ND | 8.00 | 2.73 | 4.70 | 0.01 |
| GLUCOSE | 0.34 | 0.68 | ND | ND | ND | 0.34 | 2.77 | 4.73 | 0.01 |
| GLUCONATE | 0.51 | 0.88 | ND | 0.26 | ND | 0.37 | 3.01 | 2.45 | ND |
| LACTOSE | 0.34 | 0.76 | ND | ND | ND | 9.40 | 2.58 | 4.32 | 0.77 |
| MANNITOL | 0.36 | 0.74 | ND | ND | ND | 1.40 | 1.65 | 4.26 | 0.03 |
| RHAMNOSE | 0.34 | 0.75 | ND | 0.72 | ND | 2.90 | 1.80 | 4.20 | ND |
| SORBITOL | 0.35 | 0.73 | ND | ND | ND | 0.80 | 1.66 | 3.84 | ND |
| TREHALOSE | 0.35 | 0.80 | ND | ND | ND | 8.40 | 2.66 | 4.51 | 0.05 |

*The metabolic acid products are designated as follows: ACET = acetic acid; PROP = propionic acid; and LACT = lactic acid.
ND = Not Detected (Less than 0.01 mg/ml)

Volatile and non-volatile fatty acids were determined by gas-liquid chromatographic procedures as described by Holeman and Moore (*Anerobe Laboratory Manual,* 4th edition, Department of Anaerobic Microbiology, Virginia Polytechnic Institute and State University, Blacksburg, Va., 24061).

The presently preferred best mode of this invention is the cultivation of the two bacterial strains in a nutrient growth medium sufficient to provide for a stable co-culture using the two broth media previously described or in the media described in the following Examples.

Specifically, a mixed culture of two bacterial strains (*L. casei* CLS917 and *V. criceti* 1218 is cultivated in a growth medium containing a carbohydrate substrate that strain CLS917 can ferment. Such substrates include but are not limited to mono- and di-saccharides and complex polysaccharides. Additionally, it is preferable that the growth medium also contains a source of vitamins and/or amino acids as are present in a 0.1 to 2.0% solution of the extract of yeast cells. A low concentration of a non-inhibiting, nontoxic salt of carbonic acid is preferably added to a 60 millimolar final concentration.

The conditions of the fermentation include: a temperature range generally between 20°-40° C., but preferably between 35°-40° C.; a means of agitating the fermentation mixtue at speed of up to 400 revolutions per minute, but preferably in the range of 150-250 revolutions per minute; and a pH generally in the range of 4.0 to 9.0, but preferably in the range of 5.5 to 6.0 for optimum propionic acid production. Additionally, the growth medium should preclude dissolved oxygen by preventing air flow or exchange of gases which could result in an increase in the concentration of dissolved oxygen and thereby interfere with anaerobic metabolism. Generally, the rate of the fermentation of substrate is approximately 1 to 10 millimoles per hour, preferably at least 5 millimoles per hour.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever. In the following Examples, the temperatures are set forth uncorrected in degrees Celsius; unless otherwise indicated, all parts and percentages are by weight.

EXAMPLE 1 pH Control of Fermentation

The pH of the fermantation must be maintained within the range of generally pH 5.0 to 9.0 or preferably 5.3 to 7.3 Any of several compounds acting as a Lewis Base can be used for this purpose. Hydroxides of ammonium (this includes ammonia gas, which hydrates in aqueous solutions to form ammonium hydroxide), sodium, calcium, or potassium salts can be used without deleterious effects on the fermentation. However, the divalent inorganic metal oxides, e.g. calcium hydroxide (and the corresponding oxides which hydrate in aqueous solution to form the corresponding hydroxide) appear to function better as a pH control agent than the monovalent cation hydroxdies.

In this experiment, the two strains (CLS917 and 1218) were cultivated in three liters of a medium containing (as final concentrations based on the medium): lactose, (2%), supplied as either whole whey or ultrafiltered whey permeate; yeast extract, (1.0%); and 60 millimolar of carbonate buffer of the same cation as the hydroxide (except in the case of ammonium hydroxide and ammonium gas, where calcium carbonte was used). The conditions of the fermentation included a temperature of 38° C., maintenance of pH between 5.5 and 6.0 by the automatic or manual addition of pH control agent, and continuous stirred agitation in a New Brunswick Fermenter at a speed of 200 revolutions per minutes. Aliquots were removed at the beginning of the fermentation and at 4, 8, 12, 24, and 48 hours during the fermentation. These samples were analyzed for acetic (ACET), propionic (PROP) and lactic (LACT) acids using the methodology previously described. Concentrations (in mg/ml) of these metabolic acid products from the 24 hour samples are presented in Table 3.

TABLE 3

| CO-CULTIVATION OF STRAINS CLS917 AND 1218 | | | |
|---|---|---|---|
| LEWIS BASE USED TO MAINTAIN pH (units in mM) | ACET | PROP | LACT |
| | units in mg/ml | | |
| AMMONIUM HYDROXIDE | 4.60 | 7.89 | 0.22 |
| AMMONIA GAS | 5.75 | 8.28 | 0.23 |
| CALCIUM HYDROXIDE | 7.32 | 11.48 | 0.02 |
| POTASSIUM HYDROXIDE | 4.54 | 7.18 | 0.24 |
| SODIUM HYDROXIDE | 4.62 | 8.36 | 0.20 |

EXAMPLE 2

Maintenance of Anaerobiosis

Both strains CLS917 (*L. casei*) and 1218 (*V. criceti*) are anaerobic bacteria in that they do not grow (1218) or grow welll (CLS917) in the presence of oxygen. However, under general conditions of fermentation in which a fresly steam sterilized medium is allowed to equilibrate to the temperature of the fermentation prior to inoculation with microorganisms, oxygen is effectively precluded. Thus a reducing agent, a chemical compound that can complex with dissolved oxygen, was not required for the effective fermentatin of lactose substrate to propionic acid. Additionally, the use of an inert gas (nitrogen, helium, carbon dioxide, etc.) was not required to fill the headspace (that space above the surface of the fermentation medium to the top of the vessel) to prevent the dissolution of atmospheric oxygen into the fermentation medium. Inert gas is not required during the fermentation of these two strains because strain 1218 regularly produces 1.5 moles of carbon dioxide for each mole of dissaccharide (and 0.75 moles for each mole of monosaccharide) fermented. Because strain 1218 (*V. criceti*) is an obligate anaerobe, care must be taken not to oxidize the fermentation medium by spraying or bubbling air or oxygen.

In this experiment the two strains (CLS917 and 1218) were cultivated in three liters of a medium containing lactose, (2%), supplied as either whole whey or ultrafiltered whey permeate; yeast extract, (1.0%); and 60 millimolar calcium carbonate. The conditions of the fermentation included a temperature of 38° C., maintenance of pH between 5.5 and 6.0 by the automatic or manual addition of pH control agent, and continuous stirred agitation in a Cell Stir Jar (Bellco Glass Co.) at a speed of 200 revolutions per minute. Aliquots were removed at the beginning of the fermentation and at 4, 8, 12, 24, and 48 hours during the fermentation. These samples were analyzed for acetic (ACET), propionic (PROP) and lactic (LACT) acids using the methodology previously described. Concentrations of these metabolic acid products from the 24 hour samples in which either a reducing agent, inert gas or neither were used, are presented in Table 4. It is evident from these data that standard fermentation preparations are sufficient under the conditions employed to prevent toxic concentrations of dissolved oxygen in the fermentation medium.

TABLE 4

OXYGEN PROTECTION EFFECTS ON METABOLIC ACID PRODUCTION

| OXYGEN PROTECTION | ACET | PROP | LACT |
|---|---|---|---|
| | units in mg/ml | | |
| Cystein hydrochloride (0.05%, final concentration) and the use of carbon dioxide to fill the headspace | 5.84 | 8.28 | 0.13 |
| Cystein hydrochloride only (0.05% final conc.) | 6.14 | 8.69 | 0.89 |
| No cysteine hydrochloride or carbon dioxide | 5.15 | 7.31 | 0.05 |

EXAMPLE 3

Fermentation Parameters Affecting Metabolic Acid Products

Strains of *V. criceti* demonstrate a sensitivity to low pH, dissolved oxygen, or temperatures exceeding 40° C. in the fermentation medium. Thus, for example, an adjustment of the pH to values below about 5.3–5.5, either by the addition of a Lewis acid or by the failure to maintain pH at a level greater than about 5.3–5.5, the metabolism of the Veillonella strains precludes further oxidation of lactic acid to propionic acid and acetic acid with the elaboration of carbon dioxide and hydrogen gases. Under conditions in which the co-culture is exposed to a pH of less than about 5.3–5.5, temperatures exceeding 40° C., or dissolved oxygen, the Lactobacillus continue to ferment the carbohydrates substrate to lactic acid but the Veillonella are unable to oxidize the lactic acid to additional products.

Any desired ratio of propionic acid to lactic acid can be produced by manipulation of the conditions of the fermentation, with or without the subsequent inclusion of additional substrate. This Example demonstrates the effects on the production of metabolic acid products by the variation of pH. In this experiment, the two strains (CLS917 and 1218) were cultivated in three liters of a medium containing lactose (2%) supplied as whole whey; yeast extract (1.0%); and 60 millimolar calcium carbonate. The conditions of the fermentation included a temperature of 38° C., maintenance of pH between 5.5 and 6.0 during the first 24 hour period by the automatic or manual addition of ammonium hydroxide, and continuous stirred agitation in a New Brunswick Fermenter at a speed of 200 revolutions per minute. Aliquots were removed at the beginning of the fermentation and at 8, 24, 32, and 48 hours during the fermentation. The results are summarized in Table 5:

TABLE 5

EFFECTS OF pH ON METABOLIC ACID PRODUCTS

| Time of Sample: (Hours) | ACET | PROP | LACT | |
|---|---|---|---|---|
| | | (mg/ml) | | |
| 0 | 0.09 | 0.01 | 0.24 | |
| 8 | 0.83 | 1.04 | 0.00 | |
| 24 | 2.05 | 3.78 | 6.90 | (additional lactose substrate added; the pH was allowed to drop to 5.1) |
| 32 | 1.88 | 3.51 | 6.90 | (subsequent propionic and acetic acids are produced at a lower concentration than was initially observed) |
| 48 | 2.00 | 4.01 | 28.04 | (the final ratio of propionic acid to lactic acid is 0.14 compared with 48.8 found under optimal conditions as demonstrated in Example 4) |

EXAMPLE 4

Use of Whole Sweet Whey as Substrate

Whole sweet cheese whey was used in a fermentation medium to which the two strains CLS917 and 1218 were added. In 250 liters of a medium containing lactose, (4%), supplied as whole whey (5%, with 2.5% added in the beginning of the fermentation and 2.5% added after 24 hours); yeast extract, (1.0%); and 60 millimolar calcium carbonate. The conditions of the fermentation included a temperature of 38° C., maintenance of pH between 5.5 and 6.0 by the automatic or manual addition of calcium hydroxide, and continuous stirred agitation in a New Brunswick Fermenter at a speed of 200 revolutions per minute. Aliquots were removed at the beginning of the fermentation and at 16, 24, 32, and 48 hours during the fermentation. These samples were analyzed for acetic (ACET), propionic (PROP) and lactic (LACT) acids using the methodology previously described. Concentrations of these metabolic acid products from the 24 hour samples are presented in Table 6.

TABLE 6
FERMENTATION OF LACTOSE IN WHOLE SWEET WHEY

| Time of Sample: (Hours) | ACET | PROP (mg/ml) | LACT |
|---|---|---|---|
| 0 (initial concentration of lactose 2%) | 0.11 | 0.00 | 1.35 |
| 16 | 7.05 | 9.58 | 0.35 |
| 24 (additional lactose 2%) | 8.02 | 10.80 | 0.12 |
| 32 | 9.76 | 12.96 | 18.74 |
| 48 | 14.72 | 20.00 | 0.41 |

EXAMPLE 5

Industrial Production of Propionates from Whole Sweet Whey

A pilot plant production of calcium propionate by the fermentation of whole sweet whey was conducted in the following medium: lactose, (4%), supplied as whole sweet whey present initially at 2.5% with a subsequent addition of 2.5% after 16 hours; yeast extract (Amber 510), (1.0%); and calcium carbonate (Huber-Carb S-3 ™), (0.6%). The conditions of the fermentation included: maintenance of the pH between 5.5 and 5.7 by the addition of calcium hydroxide manually as necessary; temperature of 38° C. (±1.0 degree); and agitation of approximately 200 revolutions per minute. Fermentation was conducted in 35 liter working volume stainless steel, sterilized in place fermenters.

Following fermentation, the bacterial cells were removed by microfiltration through a Romican hollow fiber membrane having a 50,000 dalton cutoff pore size and the permeate was decolorized in an activated carbon slurry, concentrated by flash evaporation, and spray dried in a tower type drier (air inlet temperature 150°–160° C.; air outlet temperature 90°–100° C.) to a free flowing, off-white powder. The chemical and physical characteristics of this fermentation product are shown in Table 7.

TABLE 7
TYPICAL ANALYSIS OF FERMENTATION PRODUCT

| | |
|---|---|
| Bulk Density (grams/cubic centimeter) | 0.03 |
| Moisture (%) | 8.1 |
| pH of 1% Solution | 6.34 |
| Solubility (grams/100 ml water) @ 25° C. | 33.00 |
| Solubility (grams/200 ml water) @ 70° C. | 32.40 |
| Crude fiber content (%) | <0.10 |
| Acid detergent fiber content (%) | <0.10 |
| Ash (%) | 55.3 |
| Crude fat (%) | <1.0 |
| Crude protein (%) | 11.10 |
| Subtotal | 66.40 |
| Carbohydrate (by difference) (%) | 33.60 |
| Soluble carbohydrate (by gas-liquid chromotography) (%) | |
| Fructose | ND |
| Glucose | <1.00 |
| Galactose | <1.00 |
| Lactose | <1.00 |
| Sucrose | ND |
| Short chain fatty acids (volatile) | |
| Calcium acetate (measured as acetic acid) (%) | 37.0 |
| Calcium propionate (as propionic acid) (%) | 42.20 |
| Short chain fatty acids (nonvolatile) | |
| Calcium lactate (as lactic acid) (%) | <2.00 |
| Calcium succinate (as succinic acid) (%) | ND |

TABLE 7-continued
TYPICAL ANALYSIS OF FERMENTATION PRODUCT

| | |
|---|---|
| Vitamins (milligrams/100 grams) | |
| Thiamine | <0.10 |
| Riboflavin | <0.10 |
| Pyridoxine | <0.10 |
| Cobalamin | <0.01 |
| Niacin | <0.10 |
| Minerals (%) | |
| Calcium | 16.69 |
| Phosphorous | 0.19 |
| Sodium | 1.15 |
| Magnesium | 0.29 |
| Subtotal | 18.32 |
| Minerals (parts per million) | |
| Aluminum | 65.48 |
| Barium | 3.45 |
| Boron | 6.58 |
| Chromium | 3.57 |
| Copper | 2.91 |
| Iron | 31.34 |
| Manganese | 3.98 |
| Strontium | 78.76 |
| Zinc | 8.07 |
| Subtotal | 204.15 |

EXAMPLE 6

Fermentation of Ultrafiltered Sweet Whey

The lactose present in ultrafiltered sweet whey was also used as substrate in the fermentation of propionic acid by a co-culture of strains CLS917 and 1218. A fermentation was conducted in the following medium: lactose (2%) supplied as dried sweet whey permeate (ultrafilter size exclusion of 30,000 daltons) and yeast extract (1.0%) and $CaCO_3$ (0.6%). Fermentation conditions included a temperature of 38° C., maintenance of pH between 5.5 and 6.0 by the automatic or manual addition of ammonium hydroxide, and continuous stirred agitation in a New Brunswick Fermenter at a speed of 200 revolutions per minute. Aliquots were removed at the beginning of the fermentation and at 4, 8, and 24 hours during the fermentation. These samples were analyzed for acetic (ACET), propionic (PROP) and lactic (LACT) acids using the methodology described in the preceding example. Concentrations of these metabolic acid products from the 24 hour samples are presented in Table 7.

TABLE 8
PRODUCTION OF PROPIONIC ACID FROM ULTRAFILTERED SWEET WHEY

| Time of Sample | ACET | PROP (mg/ml) | LACT |
|---|---|---|---|
| 0 | 0.17 | 0.05 | 1.17 |
| 4 | 0.92 | 0.93 | 1.68 |
| 8 | 2.59 | 3.67 | 4.12 |
| 24 | 7.50 | 9.56 | 0.25 |

EXAMPLE 7

Use of Cellobiose as Feedstock

While lactose is the presently preferred substrate for use in the present invention, many other carbohydrates can serve as substrates for the production of metabolic acid products. One such carbohydrate that is frequently found in nature from non-dairy sources is cellobiose, a disaccharide resulting from the partial digestion of cellulose. Following the general procedures described with reference to Table 2 demonstrates the co-cultivation of strains CLS917 and 1218 on cellobiose with concomitant production of propionic, acetic andd lactic acids. The results are summarized in Table 9. Propionic acid is not produced to a significant concentration by either strain alone.

TABLE 9

| FERMENTATION OF CELLOBIOSE BY CO-CULTIVATION | | | | | | | | |
|---|---|---|---|---|---|---|---|---|
| | V. criceti (1218) | | | L. casei (CLS917) | | | CO-CULTURE | |
| CARBOHYDRATE: | ACET | PROP | LACT | ACET | PROP | LACT | ACET | PROP | LACT |
| CONTROL (WATER) | 0.34 | 0.79 | ND | ND | ND | 0.30 | 0.46 | 0.95 | ND |
| CELLOBIOSE | 0.36 | 0.75 | ND | 0.18 | ND | 7.40 | 3.11 | 3.92 | 1.03 |

EXAMPLE 8

Use of Propionate Fermentation Product in Bakery Studies

Calcium propionate has traditionally been used to increase the shelf-life of breads and other bakery products by inhibition of the growth of molds. A fermentation of whole sweet whey in which the cells were removed and the resulting filtrate was concentrated and spray dried analogously to the process of Example 4 was used in bakery studies to determine the effects of the calcium propionate content to inhibit the growth of mold contamination. In this study, the spray dried and free-flowing powder was used in two bakery recipes. In one recipe the dried product was added to the bread dough to a final concentration of 0.5% (on a flour weight basis) which resulted in a final calcium propionate concentration of approximately 0.25. Additional active ingredients included 0.1% monocalcium phosphate and 0.9% Teklac TM (a food grade lactosse product.) The second recipe contained only the fermentation product at a final concentration of 0.5% with a calcium propionate concentration of approximately 0.25% as the only active ingredient. A third dough was prepared which was used as the control and did not contain any active ingredients.

The results of the study demonstrated that the dried fermentation product, when used at a concentration based upon the calcium propionate content traditionally employed in bread dough recipes, was effective at inhibiting the growth of mold contamination. The first and second recipes provided loaves of bread that did not demonstrate any mold growth after storage under standard conditionss up to and including thirty days, at which time the study was terminated. The third recipe which served as the control for the experiment provided loaves of bread which demonstrated mold growth after 7 to 10 days of storage.

It is clear from this example that the use of this invention in the fermentation of the lactose present in whole sweet whey by the co-cultivation of strains CLS917 (L. casei subspecies rhamnosus) and 1218 (V. criceti) resulted in the production of calcium propionate. This fermentation product when used (in either the dried or liquid form) at a calcium propionate concentration of 0.25% (final concentration on a flour weight basis) can effectively inhibit the growth of mold contamination in bread under standard storage conditions.

The preceding examples can be repeated with similar success by substituting the generically or specifically described reactants and/or operating conditions of this invention for those specifically used in the examples. From the foregoing description, one skilled in the art to which this invention pertains can easily ascertain the essential characteristics thereof and, without departing from the spirit and scope of the present invention, can make various changes and modifications to adapt it to various usages and conditions.

Industrial Applicability

As can be seen from the present specification and examples, the present invention is industrially useful in providing a method for producing calcium propionate which has a variety of known industrial applications.

What is claimed is:

1. A simultaneously sequential anaerobic fermentation process for the in vitro production of propionic acid and acetic acid, which comprises:
   (a) selecting a stable, obligatory two-component co-culture which maintains a relatively constant ratio of species populations over multiple passages, the co-culture consisting essentially of:
      (i) a first microorganism component which homo-fermentatively converts a hexose to a first metabolic product consisting essentially of lactic acid; and
      (ii) a second microorganism component from the genus Veillonella which is metabolically incapable of assimilating said hexose and which converts the lactic acid metabolic product of the first microorganism to a second metabolic product consisting essentially of propionic acid and acetic acid;
   (b) inoculating said co-culture into an assimilable nutrient growth feedstock containing a metabolizable source of said hexose;
   (c) anaerobically fermenting said feedstock with said co-culture, at a fermentation rate of at least five millimoles per liter per hour, for a period of time and under conditions sufficient to convert a major portion of the lactic acid into a fermentation product consisting essentially of propionic acid, acetic acid, salts and mixtures thereof;
   (d) maintaining the pH of the fermentation mixture such that the Veillonella continues to ferment the lactic acid being produced by the first microorganism for a period of time sufficient to accumulate said fermentation product; and
   (e) recovering the accumulated fermentation product.

2. A process according to claim 1, wherein the hexose source is selected from the group consisting of glucose, sucrose, lactose, and mixtures thereof.

3. A process according to claim 2, wherein the hexose source is lactose.

4. A process according to claim 3, wherein the feedstock is whole whey or a clarified dairy whey lactose permeate.

5. A process according to claim 1, wherein the first microorganism is a Lactobacillus or a Streptococcus.

6. A process according to claim 5, wherein the first microorganism is a *Lactobacillus casei*.

7. A process according to claim 6, wherein the first microorganism is *Lactobacillus casei subs. rhamnosus*.

8. A process according to claim 1, wherein the Veillonella is *Veillonella criceti*.

9. A process according to claim 1, wherein the co-culture is ATCC Deposit No. 39,662 or a mutant having the identifying fermentation characteristics thereof.

10. A process according to claim 1, wherein about 5 moles of propionic acid are obtained from every 8 moles of fermented lactic acid.

11. A process according to claim 1, further comprising drying the resultant product to form a free-flowing powder.

12. A process according to claim 1, wherein residual microorganism are removed from the product prior to drying.

13. A biologically pure, stable in vitro co-culture of two microorganisms adapted to anaerobically grow together while maintaining a relatively constant ratio of species populations over multiple passages such that neither microorganism overtakes the other, said co-culture consisting essentially of:
   (i) a first microorganism component which homofermentatively converts a hexose to a first metabolic product consisting essentially of lactic acid; and
   (ii) a second microorganism component from the genus Veillonella which is metabolically incapable of assimilating said hexose and which converts the lactic acid metabolic product of the first microorganism to a second metabolic product consisting essentially of propionic acid and acetic acid;
said co-culture being adapted to the in vitro anaerobic production of propionic acid and acetic acid according to the process of claim 1.

14. A biologically pure, in vitro co-culture of a Lactobacillus microorganism and a Veillonella microorganism selected from the group consisting of ATCC Deposit No. 39,622 and mutants having the identifying fermentation characteristics thereof.

* * * * *